United States Patent [19]
Webster, Jr.

[11] Patent Number: 4,554,928
[45] Date of Patent: Nov. 26, 1985

[54] ELECTROPHYSIOLOGICAL SWITCHING UNIT

[76] Inventor: Wilton W. Webster, Jr., 1388 Crest Dr., Altadena, Calif. 91001

[21] Appl. No.: 533,266

[22] Filed: Sep. 16, 1983

[51] Int. Cl.⁴ .............................................. A61B 5/04
[52] U.S. Cl. ............................. 128/709; 128/419 PG
[58] Field of Search ............... 128/630, 695, 696, 709, 128/710, 731, 786, 783, 419 D, 419 PG, 419 R, 420 R, 421, 422, 423 R, 379; 361/350, 351, 353

[56] References Cited
U.S. PATENT DOCUMENTS

| | | | |
|---|---|---|---|
| 1,597,061 | 8/1926 | Cultra | 128/423 R |
| 2,712,309 | 7/1955 | Offner | 128/731 |
| 3,058,458 | 10/1962 | Daneman | 128/709 |
| 3,610,250 | 10/1971 | Sarbacher | 128/379 |
| 3,699,970 | 10/1972 | Brindley | 128/419 R |
| 3,814,105 | 6/1974 | Howard et al. | 128/419 D |
| 3,848,608 | 11/1974 | Leonard | 128/419 R |
| 3,850,161 | 11/1974 | Liss | 128/422 |
| 4,037,586 | 7/1977 | Grichnik | 128/731 |
| 4,235,242 | 11/1980 | Howson | 128/695 |
| 4,379,462 | 4/1983 | Borkan et al. | 128/786 |
| 4,390,023 | 6/1983 | Riss | 128/421 |

FOREIGN PATENT DOCUMENTS

| | | | |
|---|---|---|---|
| 2213757 | 3/1972 | Fed. Rep. of Germany | 128/423 R |
| 1115018 | 5/1968 | United Kingdom | 128/731 |

Primary Examiner—William E. Kamm
Attorney, Agent, or Firm—Christie, Parker & Hale

[57] ABSTRACT

There is provided a switching unit for interconnecting the leads of a plurality of multiple-electrode catheters, stimulators and recorder channels. The switching unit comprises electrode switch pairs arranged in columns and rows. A separate stimulator is associated with each column and a separate electrode catheter is associated with each row of electrode switch pairs. Each electrode switch of a row is a multiple position switch and is connected to the electrode catheter associated with that row. The electrode switch pairs designate a pair of electrodes which can be monitored by a recorder channel associated with that electrode switch pair or which can be used to deliver an electrical impulse from a stimulator associated with the column of that electrode switch pair. Each column has a stimulator row-selector switch for determining which electrode switch pair, if any, of that column will be used to deliver such an electrical impulse.

17 Claims, 6 Drawing Figures

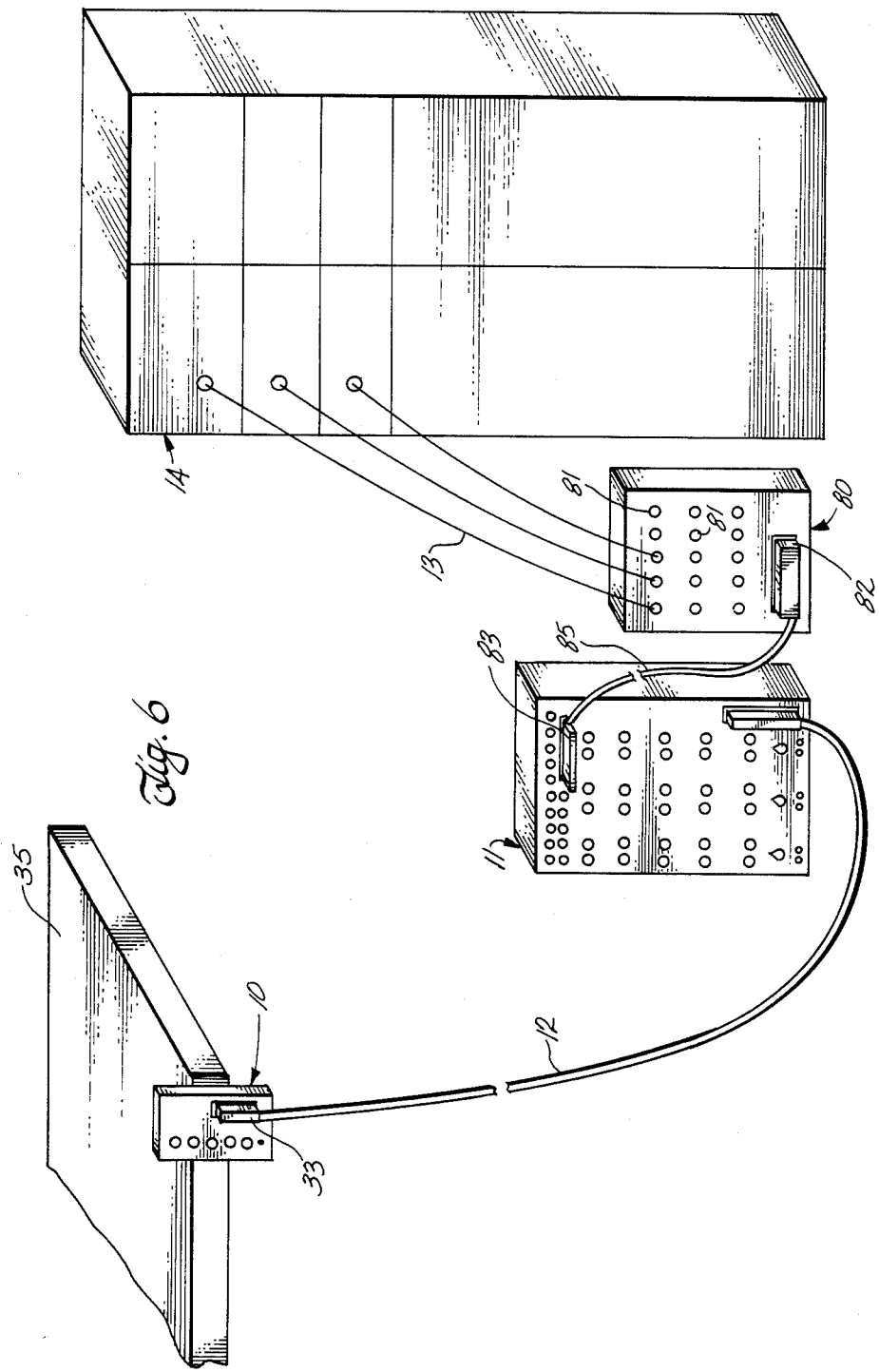

ELECTROPHYSIOLOGICAL SWITCHING UNIT

FIELD OF THE INVENTION

This invention relates to electrophysiological testing equipment and more particularly to a switching unit for interconnecting a series of multiple electrode catheters and patient reference electrodes with stimulating units and recorder channels and providing a visual display of such interconnections for easy identification.

BACKGROUND OF THE INVENTION

Multiple electrode catheters are used in electrophysiological testing for evaluating and treating heart arrhythmias. Such techniques are used to record electrical impulses intrinsic to the heart at various locations in the heart as well as to induce extrinsic electrical impulses to the heart at such various locations and to record electrical signals responsive to the delivered electrical impulses.

In such a procedure, the electrode leads of such a multiple electrode catheter must be connected to a recorder and to a stimulator, i.e., an electrical impulse generator. The present method for interconnecting catheter leads, patient reference leads and recorder leads is to connect the leads to a number of switches, each having selector positions for designating every electrode. In other words, if there are five catheters with a total of 30 electrodes plus a patient reference electrode, each switch would have 31 selector positions. In such switches, the selector position number is related to the catheter electrodes in an arbitrary manner which can vary from procedure to procedure. This makes it very difficult to keep track of which electrode of the various catheters is related to a specific selector position. Such difficulty can lead to confusion and error and the possibility of faulty evaluations of the recorded data.

The typical method for using one or more electrodes to deliver an electrical impulse is to manually disconnect those leads from the switches and connect them to the stimulator leads. Such manual connecting and disconnecting of electrode leads can also lead to confusion and error. If error results, the heart may be stimulated with an electrode which is not desired, resulting in recorded data which could be misleading and possibly a danger to the patient. At the very least, changing such connections is time consuming.

SUMMARY OF THE INVENTION

This invention provides a switching unit for interconnecting catheter electrode leads of a plurality of electrode catheters, stimulator leads, a patient reference lead and recorder leads for monitoring electical impulses in the heart and for delivering electrical impulses to the heart by select electrodes or of specific catheters. The switching unit provides an accurate visual display of which pairs of electrodes of which catheter are monitored by a specific recorder channel and which electrode pair is being used to deliver an electrical impulse to the heart. The switching unit also enables the rapid and safe switching of the particular electrodes monitored by a particular recorder channel or used for delivery of the electrical impulse.

The switching unit comprises separate input connectors for receiving the leads of at least one stimulator, a patient reference electrode lead and the leads of the catheter electrodes plus patch cords for connecting the switching unit to a recorder.

The switching unit comprises a number of rows of electrode switch pairs equal to the number of electrode catheters. Each switch pair of a row is electrically connected to a particular electrode catheter.

Each electrode switch of a switch pair has a number of selector positions equal to the number of electrodes of the catheter plus an extra position designated REF. Each selector position is separately connected to one electrode of the catheter and the REF position is connected to the patient reference electrode.

Each electrode selector switch pair is connected to a recorder channel. The recorder channel monitors the voltage drop from the catheter electrode designated by the first electrode switch of the switch pair and the catheter electrode designated by the second electrode of the switch pair.

A multi-position stimulator row-selector selector switch is connected with each pair of stimulator leads and has a number of selector positions equal to the number of rows of electrode switch pairs plus an extra position designated OFF.

Selection of a selector position on the stimulator row-selector switch determines which electrode switch pairs and, hence, which catheter will be used to deliver an electrical impulse to the heart. Selection of particular selector position on the electrode switch of the designated electrode switch pair determines which electrodes of the catheter will deliver the electrical impulse to the heart.

In a preferred embodiment of the invention, the switch box comprises means for receiving the leads of five six-electrode catheters and a patient reference electrode lead and three pairs of stimulator leads. The switch box forms a matrix of switches having three columns and six rows. Each column has five rows formed by electrode switch pairs, each row being associated with a particular catheter, and a sixth row formed by a stimulator row-selector switch. Each of the fifteen electrode switch pairs is connectable to a separate recorder channel.

Such a switch box allows monitoring of the voltage drop across up to fifteen pairs of catheter electrodes and between any electrode and the patient reference electrode plus the capability of delivering up to three electrical stimuli simultaneously to the heart. Further, the switch box visually displays which catheter and which electrodes of that catheter are being monitored by a particular recorder channel or are being used to deliver an electric impulse to the heart.

BRIEF DESCRIPTION OF THE DRAWINGS

These and other features and advantages of the present invention will be better understood by reference to the following detailed description when considered in conjunction with the accompanying drawings wherein:

FIG. 6 is a schematic view of another preferred switching apparatus comprising a patch cord connecting unit.

DETAILED DESCRIPTION

Figure 1:
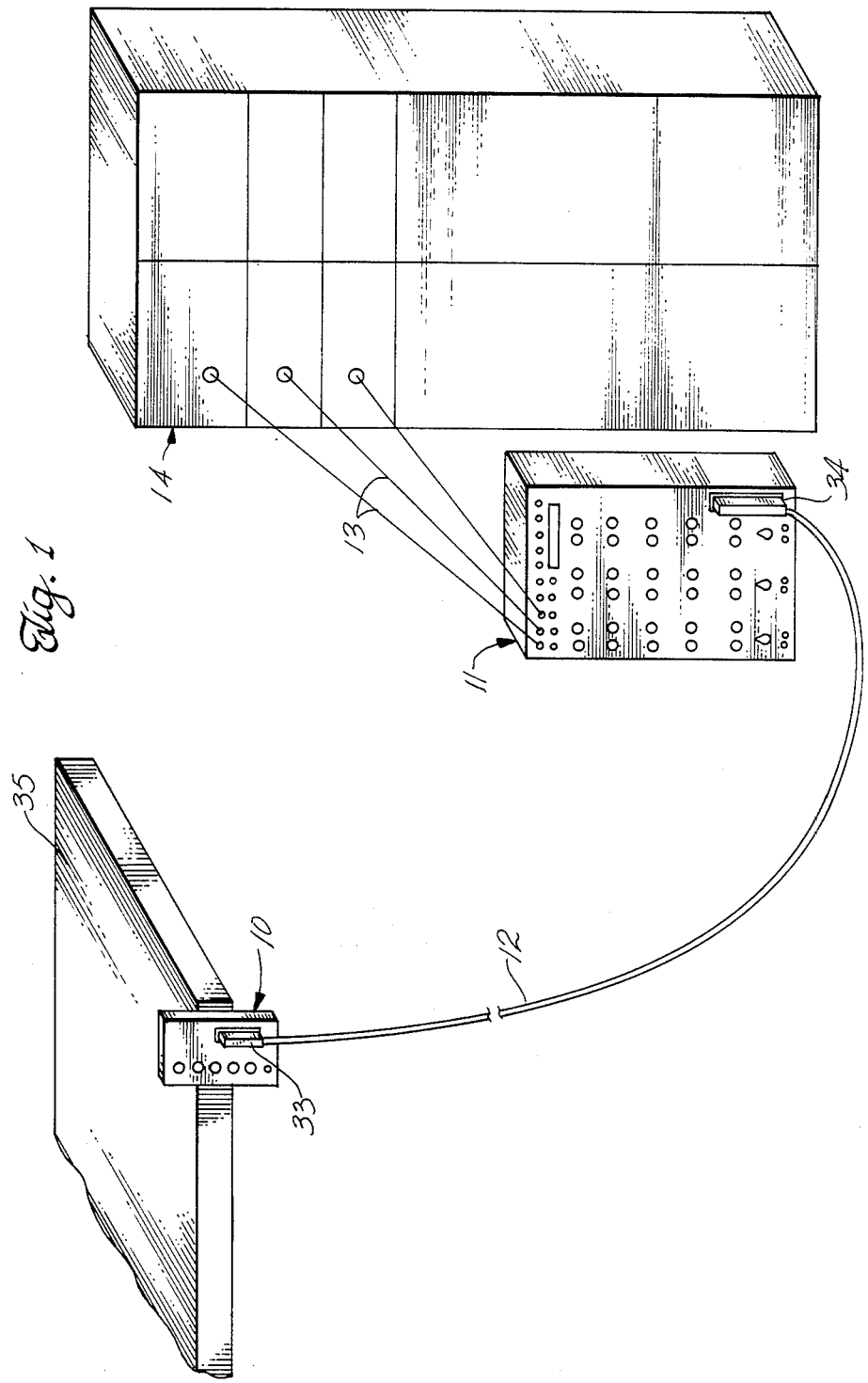
FIG. 1 is a schematic view of a preferred switching apparatus.

With reference to FIG. 1, there is shown a preferred switching apparatus for use with up to five six-electrode cathethers. The switching apparatus comprises a remote catheter plug-in unit 10 for receiving the leads of the electrode catheters, a switch box 11, a connector cable 12 for connecting the switch box 11 to the remote catheter plug-in unit 10 and a plurality of patch cords 13 for connecting the switch box 11 to a recorder 14.

The remote catheter plug-in unit 10 is designed to be mounted near the patient. It functions to connect the leads of five electrode catheters to the switch box 11 in an orderly fashion through a single connector cable 12. This eliminates the chance of confusion and mistake with respect to which electrodes of the various catheters are associated with specific electrode leads. Such confusion can easily arise when working with multiple catheters with numerous electrode leads.

Figure 2:
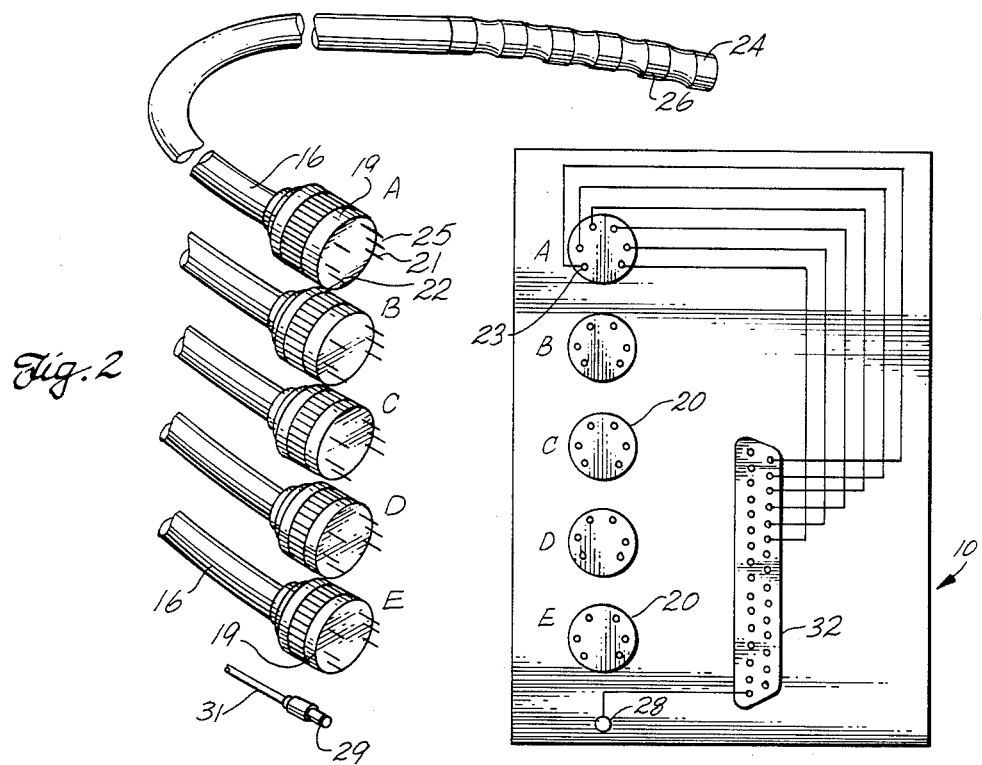
FIG. 2 is a schematic view of a preferred remote catheter plug-in unit showing the electrical connections between one six-pin female connector and the 31-pin female connector.

With reference to FIG. 2, the electrode catheters 16 are designated A through E. The leads of each electrode end in a six-pin male connector 19, each pin being electrically connected to one of the six electrodes of that catheter. The remote catheter plug-in unit 10 has five six-pin female connectors 20, also designated A through E, for receiving the six-pin male connectors 19 of the five electrode catheters 16.

The six pins of the male connectors are arranged so that they can be plugged into the female connectors in only one orientation. For example, the pins may be spaced-apart evenly in a circular arrangement with a single large gap between the first pin 21 and the sixth pin 22. In this way, the first pin 21 of the male connector 19 will always be plugged into the first pin input 23 of the six-pin female connector 20.

The pins of each six-pin male connector 19 are connected to the electrodes of that catheter in sequence beginning with the electrode at the catheter tip. That is, the first pin 21 of catheter A is connected to the first electrode 24 of catheter A, the second pin 25 is connected to the second electrode 26 and so on. When plugged into the remote plug-in unit, the first pin input 23 of the six-pin female connector is always electrically connected to the first electrode 24 of that catheter. Similarly, the second through sixth pin input are electrically connected to the second through sixth electrodes respectively.

The remote catheter plug-in unit also has an input jack 28, e.g., a banana jack, for receiving the input plug 29 of a patient reference electrode 31.

The pin inputs of the five six-pin female catheter connectors 20 are connected in sequence to separate and specific pin inputs of a 31-pin female connector 32. For example, as shown in FIG. 2, the pin inputs of the six-pin female catheter connector labeled A are connected to six specific pin inputs of the 31-pin female connector 32. The six pin inputs of the six-pin catheter connectors B through E are likewise connected to specific pin inputs of the 31-pin female connector. The patient reference input jack 28 is connected to the remaining pin input of the 31-pin female connector 32. Each pin input of the 31-pin female connector thereby electrically connected to a specific electrode of a specific catheter or the patient reference electrode.

Again with reference to FIG. 1, the connector cable 12 is a shielded cable having 31-pin male connectors 33 and 34 at opposite ends. Corresponding pins of the male connectors 33 and 34 are electrically connected by means of wires extending the length of the cable. One end is plugged into the 31-pin female connector 32 of the remote catheter plug-in unit 10. The other end of the connector cable is plugged into a corresponding 31-pin female connector on the switch box 11. The length of the connector cable is not critical, but is selected to be sufficient to extend from the remote plug-in unit adjacent the patient table 35 to the location of the switch box 11 which is determined by the physician.

Figure 3:
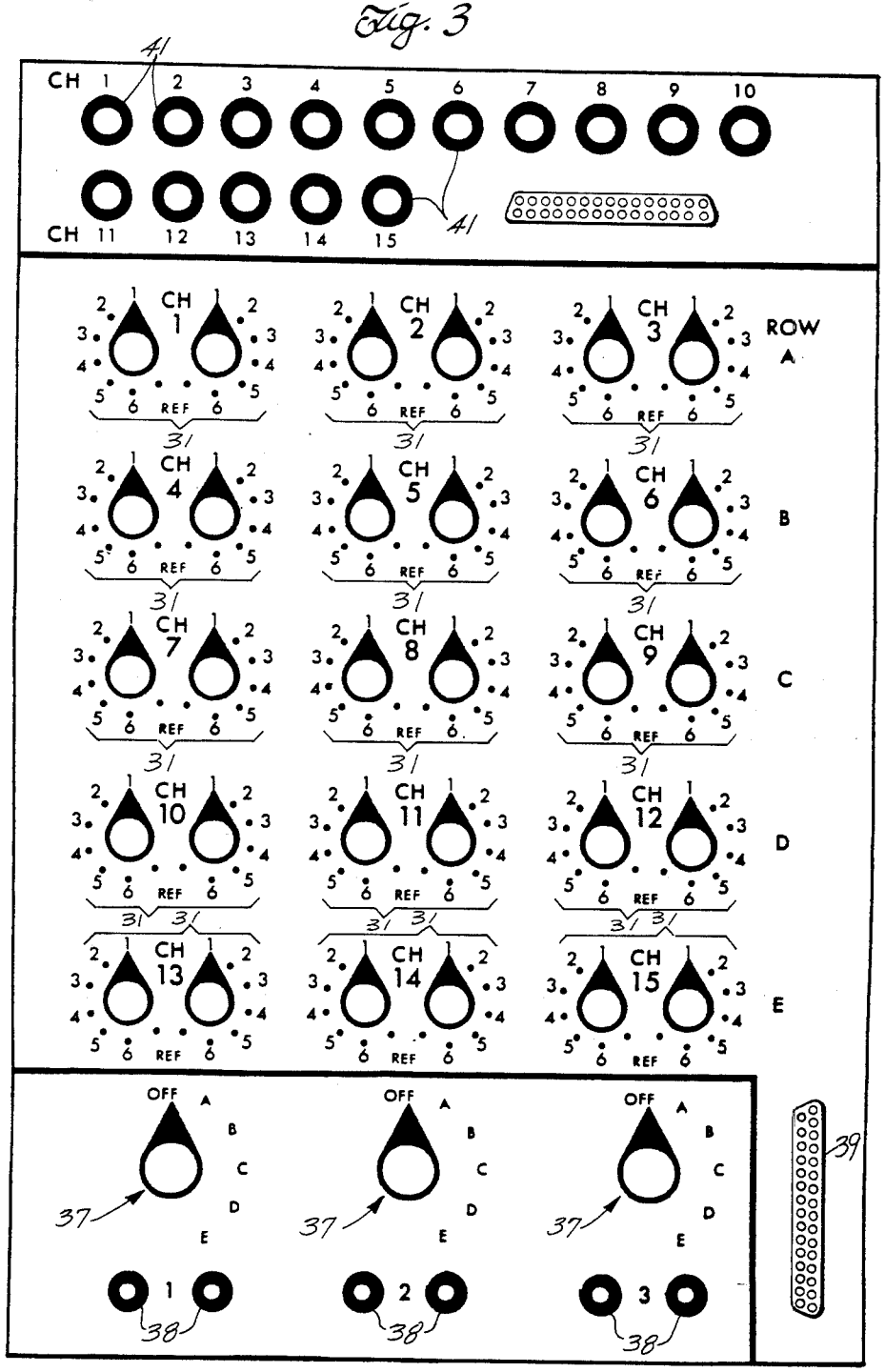
FIG. 3 is a schematic view showing the electrical connections between the electrode switch pairs of Row A and the 31-pin female connector of the switching unit.

As shown in FIG. 3, the switch box 11 comprises three columns of switches. Each column has five electrode switch pairs 31 and a stimulator row-selector switch 37. The columns are aligned to generate six rows. The first five rows labeled A through E each comprise three electrode switch pairs 31. The row letters correspond to the letter designations of the catheters. The sixth row comprises three stimulator row-selector switches 37. A pair of stimulator input jacks 38 are associated with each stimulator row-selector switch 37. The stimulator row-selector switches 37 and associated stimulator input jacks 38 are labeled 1 through 3 and are electrically connectable to first, second and third sets of stimulator or pacing leads. The catheter switch pairs 36 are connectable to separate recorder channels and are labeled CH1 through CH15 for recorder channel identification.

The switch box 11 has a 31-pin female connector 39 for receiving the 31-pin male connector 34 of the connector cable 12. When connected to the remote plug-in unit 10 by the connector cable 12, each pin input of the 31-pin female connector 39 of the switch box 11 is electrically connected to the individual electrodes of the electrode catheters in the same sequence as the 31-pin female connector 32 of the remote plug-in unit 10.

The switch box further comprises fifteen phone jacks 41 for connecting the switch box 10 to the recorder 14 via patch cords 13.

Figure 4:
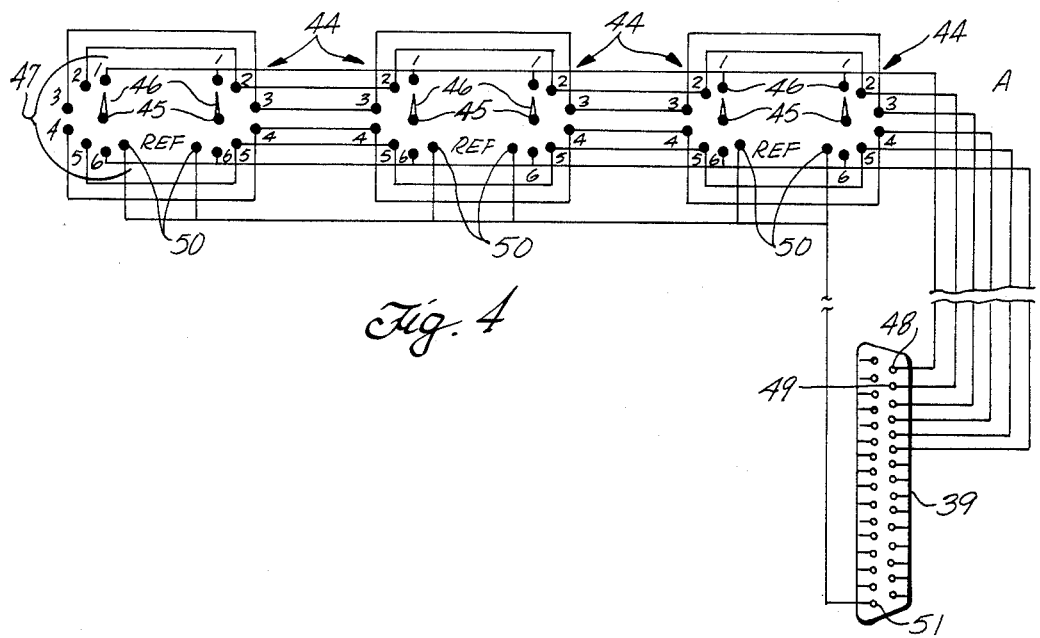
FIG. 4 is a top view of the switching unit.

With reference to FIG. 4, each electrode switch 44 of the electrode switch pairs 36 is a seven position switch having a pole 45, an electrically conductive selector arm 46 and seven electrically conductive selector positions 47 labeled 1 through 6 and REF. Each of the positions are electrically connected to specific pin inputs of the 31-pin female connector 39. The selector position labeled 1 of each electrode switch in Row A is connected to pin input 48 of the 31-pin female connector 39 which, when connected to the remote plug-in unit by the connector cable 12, is electrically connected to the first electrode 24 of catheter A. The selector position labeled 2 of each electrode switch 44 in Row A is connected to pin input 49 of the 31-pin electrode of catheter A and is thereby electrically connected to the second electrode 26 of catheter A. Similarly, the third through sixth selector positions of the electrode switches of Row A are connected to the pin inputs of the 31-pin female connector 39 which, in turn, are connected to the third through the sixth electrodes of catheter A respectively.

Likewise, selector positions 1 through 6 of each electrode switch in Row B are connected to the pin inputs of the 31-pin female connector 39 which are connected to the six electrodes of catheter B beginning with the electrode at the catheter tip in a manner as described for Row A. Selector positions 1-6 of the electrode switches in Rows C, D and E are likewise connected to the pin inputs of the 31-pin female connector 59 which are in electrical communication with the electrodes of catheters C, D and E.

The seventh selector position 50 of each electrode switch in each row is labeled REF and is connected to the remaining pin input 51 which receives the pin of the connector cable 12 in communication with the patient reference electrode 31.

Figure 5:
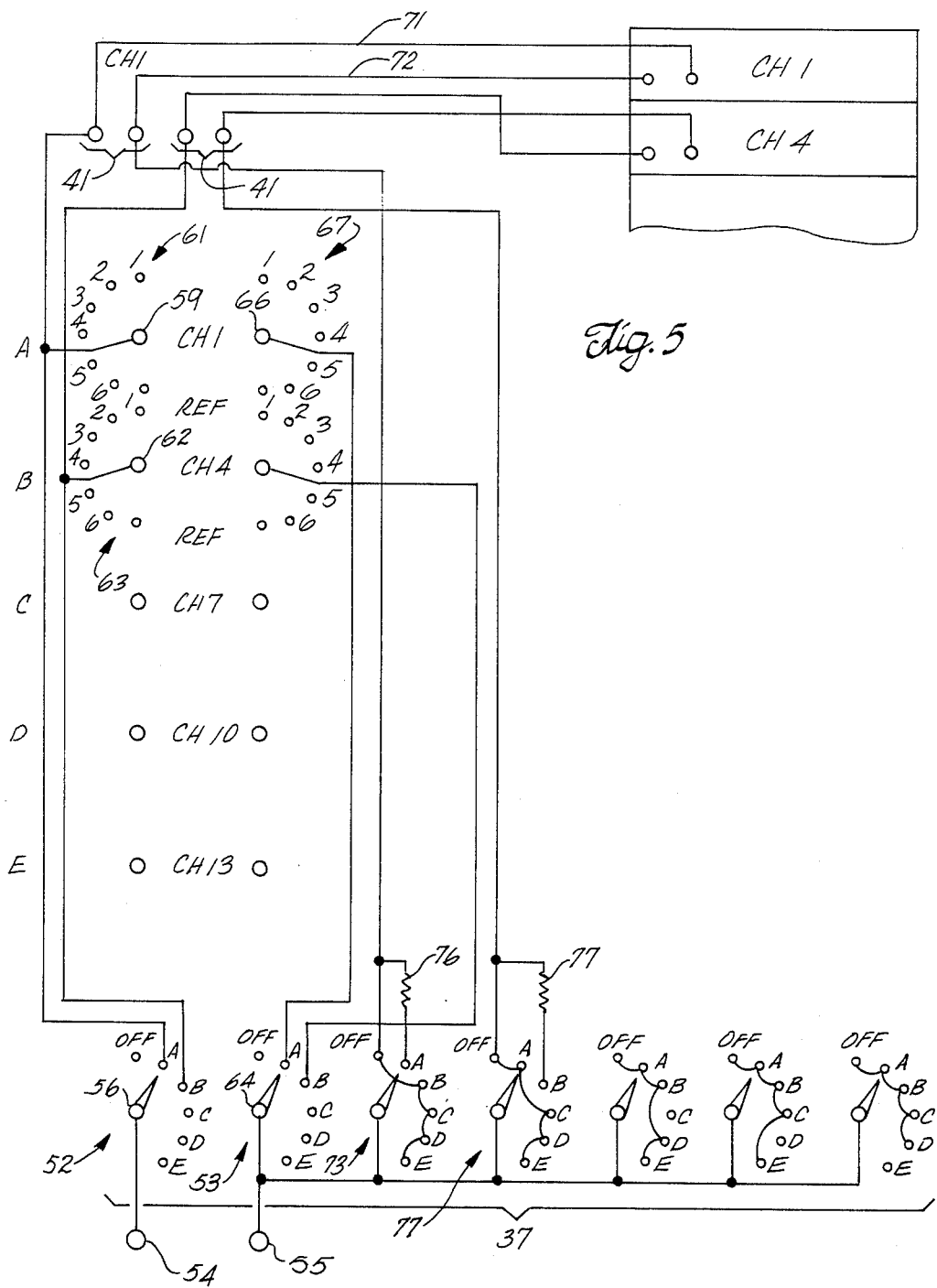
FIG. 5 is schematic view of the electrical connections between a stimulator row-selector switch, electrode switch pairs and the corresponding recorder channels.

With reference to FIG. 5, each stimulator row-selector switch 37 is a stacked multi-wafer switch, each wafer having a pole, a selector arm, and six selector positions. The selector positions are labeled OFF and A through E which correspond to the five rows of switch pairs also labeled A through E. Designation of a particular selector position results in the selector arms of all wafers being in that position.

The first two wafers 52 and 53 designate which electrode switch pair and, hence, which catheter will be used to deliver an electrical impulse from the stimulator unit whose leads are plugged into input jacks 54 and 55. The remaining five wafers are designed to allow the recorder channels to monitor signals from the non-designated switch pairs and to interrupt signals to the recorder from the designated electrode switch pair. Each of these remaining five wafers is associated with an electrode switch pair of that column, the third wafer being associated with the catheter switch pair of Row A, the fourth wafer being associated with the electrode switch pair of Row B and so on.

The pole 56 of the first wafer is electrically connected to the input jack 54 for receiving the first stimulator lead. The selector positions A-E of the first wafer are connected to the poles of the first electrode switch of the corresponding switch pairs in that column. For example, selector position A is connected to the pole 59 of the first electrode switch 61 of the electrode switch pair in Row A. Selector position B of wafer 57 is connected to the pole 62 of the first electrode switch 63 of the switch pair in Row B and so on. The OFF contact position is not connected to anything.

The pole 64 of the second wafer 53, which is not in electrical contact with the pole 56 of the first wafer 52, is connected to the input jack 55 for receiving the second stimulator lead. The selector position A of the second wafer 53 is connected to the pole 66 of the second catheter switch 67 of the switch pair in Row A. Similarly, selector positions B through E of the second wafer 53 are connected to the poles of the second catheter switch of the switch pairs in the corresponding rows.

Switching the stimulator row-selector switch 37 to selector position A thereby forms an electrical circuit from a stimulator or pacing unit through a first lead plugged into the first stimulator jack 54, through first wafer 52 of the stimulator row-selector switch 37 to the first electrode switch 61 of the electrode switch pair in Row A and then to the electrode of catheter A which is designated by the first electrode switch 61. A second circuit extends from the electrode of catheter A which is designated by the second electrode switch 67 to the second electrode switch 67, through the second wafer 53 of the stimulator row-selector switch 37 to the second stimulator jack 55 and then to the stimulator by a second stimulator lead which can be plugged into that second jack 55.

When the electrodes of catheter A are placed in contact with a conductive substance, e.g., animal tissue, there is an electrical pathway between the electrodes designated by electrode switches 61 and 67 which completes a circuit between the two stimulator leads. Hence, an electrical impulse can be transmitted between those designated electrodes.

The electrode switch pairs of all columns which are not used to deliver electrical impulses can be used to monitor and record the voltage drop across the electrodes which are designated by those electrode switch pairs.

Each recorder channel has a pair of leads, both carried by a patch cord 13 having a phone plug at its end which can be plugged into a corresponding phone jack 41 in the switch box 11. To monitor the voltage drop across the electrodes designated by a particular electrode switch pair, one lead from the recorder channel associated with that electrode switch pair is electrically connected to one of the electrodes and the other lead is connected to the other electrode. Recorder channels associated with electrode switch pairs which are designated by the stimulator row-selector switches are disconnected.

When plugged into the phone jack 41 for Recorder Channel No. 1, the first lead 71 of Recorder Channel No. 1 is electrically connected to the pole 59 of the first electrode switch 61 of the electrode switch pair of Row A designated CH1 and, hence, is in electrical contact with the electrode of catheter A designated by the first electrode switch 61. The first lead of Recorder Channels Nos. 4, 7, 10 and 13 are similarly connected to the poles of the first electrode switches of the electrode switch pairs in Rows B, C, D and E which are designated CH4, CH7, CH10 and CH13.

The second lead 72 of recorder channel 1 is connected to the third wafer 73 of the stimulator row selector switch 37 which is associated with the electrode switch pair in Row A. Likewise, the second lead of recorder channels 4, 7, 10 and 13 are connected to the fourth, fifth, sixth and seventh wafers of that stimulator row-selector switch 37.

In each of the third through seventh wafers, the pole of that wafer is connected to the second stimulator lead. The selector positions are all in electrical contact with each other except for the position which designates the electrode switch pair associated with that wafer. For example, the third wafer 73 of the stimulator row-selector switch is associated with the electrode switch pair of Row A. All of the selector positions except position A, i.e., selector positions B through E and OFF, are connected to each other and to the second lead of recorder channel 1. Selector position A is not connected to anything.

In this arrangement, when the stimulator row-selector switch 37 is moved to selector position A, the pole of the third wafer 73 is in electrical communication with the electrode of catheter A designated by the second electrode switch of the switch pair of Row A. However, there is a break in the circuit between the pole of the third wafer and Recorder Channel No. 1 which is in electrical communication only with positions B through E and OFF. When the stimulator row-selector switch is moved to positions B through E or OFF, the circuit between the pole of the third wafer 73 and Recorder Channel No. 1 is completed. Thus, Recorder Channel No. 1 which associated with the electrode switch pair in Row A designated CH1 is activated when the stimulator row-selector switch designates Rows B through E or OFF and is deactivated when the stimulator row-selector switch designates Row A.

Likewise, when the stimulator row-selector switch 37 designates Row B through E, the recorder channel associated with the electrode switch pair of the designated row will be deactivated.

In a particularly preferred embodiment of the invention, the recorder channel which is associated with the electrode switch pair used to deliver an electrical signal from the stimulator unit monitors the signals from the stimulator unit. This is accomplished by making an electrical connection from the recorder channel to the selector positions designating that electrode switch pair of the wafer which is associated with that switch pair through a resistor. For example, selector position A of the wafer 73 associated with Row A can be connected to Recorder Channel No. 1 through resistor 76. Likewise, selector position B or wafer 77 which is associated with Row B can be connected to Recorder Channel No. 4 through resistor 78 and so on. The resistors allow a small portion of the stimulator signal to bleed into the recorder channel so that the onset of the signal can be monitored.

The preceding description has been presented with reference to presently preferred embodiments of the invention shown in the accompanying drawings. Workers skilled in the art and technology to which this invention pertains will appreciate that alterations and changes in the described apparatus and structure can be practiced without meaningfully departing from the principles, spirit and scope of this invention.

For example, it is apparent that the connector cables need not be detachable from the remote plug-in unit and/or the switch box. In such an embodiment of the invention, the 31-pin connection of the remote plug-in unit and/or switch box would be unnecessary.

Connectors other than those mentioned above may also be used. Since it is generally undesirable for the leads coming from the catheters to be exposed, such leads typically end in connectors in which the leads are recessed. Such connectors can be either male or female. Additionally, nine-pin and 37-pin male and female connectors may be more readily available than six-pin and 31-pin connectors and can be used.

If desired, a patch cord connecting unit can be used so that the switch box can be positioned away from the recorder. As shown in FIG. 6, a patch cord connecting unit 80 comprises fifteen phone jacks 81 for receiving the phone plugs of fifteen recorder patch cords 13 and a 31-pin female connector 82. The switching unit 11 can be equipped with a similar 31-pin female connector 23 connected to the electrode switch pairs so that the switching unit can be connected to the patch cord connecting unit 80 and hence to the recorder channels by a single connecting cable 85.

What is claimed is:

1. A switching unit for interconnecting multiple-electrode catheter leads, stimulator leads and recorder channel leads comprising:
    at least one column of switches comprising:
        at least two electrode switch pairs each comprising first and second electrode switches, each electrode switch having a pole and multiple selector positions;
        first and second stimulator row-selector switches each comprising a pole and selector positions designating each electrode switch pairs of that column;
    means for electrically connecting the poles of the first and second electrode switches of an electrode switch pair to separate leads of a recorder channel;
    means for electrically connecting the selector positions of both electrode switches of a switch pair to the electrode leads of a multiple electrode catheter;
    means for electrically connecting the poles of the stimulator row-selector switches to separate leads of a stimulator;
    means for electrically connecting each selector position of the first stimulator row-selector switch to the pole of the first electrode switch of the electrode switch pair designated by that selector position; and
    means for electrically connecting each selector position of the second stimulator row-selector switch to the pole of the second electrode switch of the switch pair designated by that selector position.

2. A switching unit as claimed in claim 1 wherein each electrode switch of each electrode switch pair comprises an additional selector position and wherein the switching unit further comprises means for electrically connecting the additional selector position of each electrode switch to the lead of a patient reference electrode.

3. A switching unit as claimed in claim 1 wherein the first and second stimulator row-selector switches of each column are combined into a single two-pole switch.

4. A switching unit as claimed in claim 1 wherein each stimulator row-selector switch comprises an additional selector position not in electrical contact with an electrode switch.

5. A switching unit as claimed in claim 1 further comprising means for breaking the electrical connection between an electrode switch pair and a recorder channel electrically connected with that electrode switch pair when that electrode switch pair is designated by the stimulator row-selector switch.

6. A switching unit as claimed in claim 1 comprising at least two columns of switches which are arranged to form at least two rows of electrode switch pairs, and wherein the switching unit comprises means for electrically connecting every electrode switch in a row of electrode switch pairs to the leads of a multiple electrode catheter so that the selector positions of each electrode switch in that row are electrically connected the electrodes of the multiple electrode catheter in the same sequence.

7. A switching unit for interconnecting the leads of multiple electrode catheters, stimulators and recorder channels, said switching unit comprising a matrix of switches, said matrix having a select number of rows and columns wherein:
    one row comprises a number of stimulator row-selector switch pairs equal to the number of columns, each stimulator row-selector switch pair comprising first and second stimulator row-selector switches, and the remaining rows comprise a number of electrode switch pairs equal to the number of columns, each electrode switch pair comprising first and second electrode switches, and wherein each row of electrode switch pairs is associated with a separate multiple-electrode catheter, each column is associated with a separate stimulator and each electrode switch pair is associated with a separate recorder channel;

each column comprises one stimulator row-selector switch pair and a number of electrode switch pairs equal to one less than the number of rows; and wherein the stimulator row-selector switch in each column comprises a pole and selector positions designating the electrode switch pairs of that column, and the electrode switches in each row of electrode switch pairs comprise a pole and selector positions designating each electrode of the multiple electrode catheter associated with that row; and wherein the switching unit further comprises means for electrically connecting the selector positions of each electrode switch of a row to the leads of a multiple electrode catheter so that the selector positions are electrically connected to the electrodes of the catheter which they designate;

means for connecting the poles of each electrode switch pair to the leads of a separate recorder channel for monitoring electrical signals between the pair of catheter electrodes designated by each electrode switch pair;

means for electrically connecting each selector position of the first stimulator row-selector switch of a row to the pole of the first electrode switch of the electrode switch pair of that row designated by that selector position;

means for electrically connecting each selector position of the second stimulator row-selector switch of a row to the pole of the second electrode switch of the electrode switch pair of that row designated by that selector position; and means for electrically connecting the poles of the first and second stimulator row-selector switch of a column to separate leads of a stimulator.

8. A switching unit as claimed in claim 7 wherein each electrode switch of each electrode switch pair comprises an additional selector position and wherein the switching unit further comprises means for electrically connecting the additional selector position of each electrode switch to the lead of a patient reference electrode.

9. A switching unit as claimed in claim 7 wherein each stimulator row-selector switch comprises an additional selector position not in electrical contact with an electrode switch.

10. A switching unit as claimed in claim 7 further comprising means for breaking the electrical connection between an electrode switch pair of a column and the recorder channel associated with that electrode switch pair when that electrode switch pair is designated by the stimulator row-selector switch of that column.

11. A switching unit for interconnecting the leads of five six-electrode catheters and a patient reference electrode with three pairs of stimulator leads and fifteen pairs of recorder channel leads comprising a switch box which comprises:

electrode catheter lead inputs for receiving the leads of five six-electrode catheters;

a patient reference electrode lead input for receiving the lead of a patient reference electrode;

stimulator lead inputs for receiving the leads of three stimulators;

recorder channel lead inputs for receiving the leads of fifteen recorder channels;

three columns of switches, each column comprising a stimulator row-selector switch and five electrode switch pairs, said columns being arranged to form one row of stimulator row-selector switch pairs and five rows of electrode switch pairs, wherein each stimulator row-selector switch pair is associated with a separate stimulator, each electrode switch pair is associated with a separate recorder channel and each row of electrode switch pairs is associated with a separate multiple electrode catheter; and wherein each electrode switch pair comprises first and second electrode switches, each electrode switch having a pole and seven selector positions;

the stimulator row-selector switch of each column comprises first and second poles and six selector positions associated with each pole wherein the first five selector positions associated with each pole designate the five rows of electrode switch pairs in that column and wherein the sixth selector position associated with each pole of the stimulator row-selector switch is not electrically connected to an electrode switch; and wherein the switching unit further comprises:

means for electrically connecting the first pole of a stimulator row-selector switch to the stimulator lead input receiving one lead of the stimulator associated with that stimulator row-selector switch;

means for electrically connecting the second pole of a stimulator row-selector switch to the stimulator lead input receiving the other lead of the stimulator associated with that stimulator row-selector switch;

means for electrically connecting each of the first five selector positions associated with the first pole of a stimulator row-selector switch to the pole of the first electrode switch of the electrode switch pair designated by that selector position;

means for electrically connecting each of the first five selector positions associated with the second pole of the stimulator row-selector switch to the pole of the second electrode switch of the electrode switch pair designated by that selector position;

means for electrically connecting each electrode switch of a row of electrode switch pairs to the electrode catheter lead input which receive the leads of the electrode catheter associated with that row so that the first six selector positions of each electrode switch in that row are electrically connected in the same sequence to the six electrodes of that electrode catheter when the electrode catheter lead lead input receives the leads of that electrode catheter;

means for electrically connecting the seventh selector position of each electrode switch to the patient reference electrode lead input; and means for electrically connecting each electrode switch pair to the recorder channel lead inputs so that the pole of the first electrode switch of an electrode switch pair is electrically connected to one lead of the recorder channel associated with that electrode switch pair and the pole of the second electrode switch of the electrode switch pair is electrically connected to the other lead of that recorder channel when the recorder channel lead inputs receive the recorder channel leads.

12. A switching unit as claimed in claim 11 wherein the electrode catheter lead inputs and the patient reference electrode lead input of the switch box are formed by a single multiple-pin electrode input connector and wherein the switching unit further comprises means for connecting the electrode catheter leads and the patient reference electrode lead to a single multiple-pin connector for connecting with the multiple-pin electrode input connector of the switch box.

13. A switching unit as claimed in claim 12 wherein the means for connecting the electrode catheter leads and the patient reference electrode lead to a single multiple-pin connector comprises:
- a remote plug-in unit comprising electrode lead inputs for receiving the electrode catheter leads and the patient reference electrode lead, a multiple-pin input connector and means for electrically connecting the electrode lead inputs to the multiple-pin input connector; and
- a connector cable having a multiple-pin connector at one end connectable to the multiple-pin input connector of the remote plug-in unit and multiple-pin connector at its other end connectable to the multiple-pin electrode input connector of the switch box.

14. A switching unit as claimed in claim 11 wherein the recorder channel lead inputs of the switch box are formed by a single multiple-pin recorder input connector and wherein the switching unit further comprises means for connecting the recorder channel leads to a single multiple-pin connector for connecting with the multiple-pin recorder input connector of the switch box.

15. A switching unit as claimed in claim 14 wherein the means for connecting the recorder channel leads to a single multiple-pin connector comprises:
- a patch cord connecting unit comprising recorder channel lead inputs for receiving the recorder channel leads, a multiple-pin input connector and means for electrically connecting the recorder channel lead inputs to the multiple-pin input connector; and
- a connector cable having a multiple-pin connector at one end for connecting with the multiple-pin input connector of the patch cord connecting unit and multiple-pin connector at its other end for connecting with the multiple-pin recorder input connector of the switch box.

16. A switching unit as claimed in claim 11 further comprising means for breaking the electrical connection between an electrode switch pair and the recorder channel associated with that electrode switch pair when that electrode switch pair is designated by the stimulator row-selector switch of the column of the switch pair.

17. A switching unit as claimed in claim 11 further comprising means for monitoring the stimulator signal between two electrodes on the recorder channel associated with the electrode switch pair designating those two electrodes.

* * * * *